(12) United States Patent
Dos Santos et al.

(10) Patent No.: US 8,124,100 B2
(45) Date of Patent: Feb. 28, 2012

(54) INACTIVATED NODAVIRUS VACCINE

(75) Inventors: Nuno Dos Santos, Torreira (PT); Jacqueline Ireland, Scotland (GB); Andrew Cartner Barnes, Brisbane (AU); Michael Horne, Stirling (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/425,135

(22) Filed: Apr. 16, 2009

(65) Prior Publication Data

US 2009/0288179 A1  Nov. 19, 2009

Related U.S. Application Data

(63) Continuation of application No. 10/545,528, filed as application No. PCT/EP2004/001543 on Feb. 18, 2004, now abandoned.

(30) Foreign Application Priority Data

Feb. 19, 2003 (GB) .................................. 0303867.6
Aug. 28, 2003 (GB) .................................. 0320195.1

(51) Int. Cl.
*A61K 39/00* (2006.01)
*A61K 39/12* (2006.01)
*C12N 7/06* (2006.01)
*C12N 15/74* (2006.01)

(52) U.S. Cl. ..................... 424/204.1; 435/471; 435/238; 424/184.1

(58) Field of Classification Search ........................ None
See application file for complete search history.

(56) References Cited

U.S. PATENT DOCUMENTS 5,891,705 A  4/1999  Budowsky et al.
(Continued)

FOREIGN PATENT DOCUMENTS

EP  1006178 A2  6/2000
(Continued)

OTHER PUBLICATIONS

Frerichs et al., Temperature, pH and electrolyte sensitivity, and heat, UV and disinfectant inactivation of sea bass *Dicentrarchus labrax*/neuropathy nodavirus, 2000, Aquaculture, vol. 185, pp. 13-24.*

(Continued)

*Primary Examiner* — Benjamin P Blumel

(57) ABSTRACT

A vaccine against nodavirus infection in fish can be produced by inactivating the virus using an aziridine compound. This vaccine can be used to prevent Viral Nervous Necrosis (VNN) in a variety of fish species.

8 Claims, No Drawings

U.S. PATENT DOCUMENTS 6,436,702 B1     8/2002    Chi
2004/0001863 A1    1/2004    Chi

FOREIGN PATENT DOCUMENTS

WO     WO 98/45415     10/1998
WO     WO 99/50419     10/1999
WO     WO 03/050142 A1     6/2003

OTHER PUBLICATIONS

Intl Council for the Exploration of the Sea, Mariculture Committee: Rpt on the Working Group on Pathology & Diseases of Marine Organisms, Copenhagen, Denmark, Mar. 12-16, 2002.

G.N. Frerichs, et al., "Cell culture isolation of piscine neuropathy nodavirus from juvenile sea bass, *Dicentrarchus labrax*," Journ. Gen. Vir. (1996), vol. 77, pp. 2067-2071.

Bahnemann H.G. "Inactivation of viral antigens for vaccine preparation with particular reference to the application of binary ethylenimine," Vacc vol. 8, No. 4, p. 299-303, 1990.

Broo et al., Viral capsid mobility: A dynamic conduit for inactivation, 2001, PNAS, vol. 98, No. 5, pp. 2274-2277.

Frerichs et al., "Cell culture isolation of pescine neuropathy nodavirus from juvenile sea bass, *Dicentrarchus labrax*," Journ. of Gen. Virol., vol. 77, pp. 2607-2071, 1996.

Iwamoto et al., "Cloning of the fish cell line SSN-1 for piscine nodaviruses," Disease of Aquatic Organisms, vol. 43, pp. 81-89, 2000.

Skliris et al., "Induction of nodavirus disease in seabass, *Dicentrachus labrax*, using different infection models," Virus Research, vol. 63, pp. 85-93, 1999.

Skliris et al., phylogenetic and antigenic characterization of new fish nodavirus isolates from Europe and Asia, Virus Research, vol. 75, pp. 59-67, 2001.

Thiery et al., Induction of a protective immune response against viral nervous necrosis in the European Sea Bass *Dicentrarchus labrax* by using betanodavirus virus-like particles, Journal of Virology, vol. 80, No. 20, pp. 10201-10207, 2006.

\* cited by examiner

INACTIVATED NODAVIRUS VACCINE

This application is a continuation of U.S. application Ser. No. 10/545,528 filed Sep. 6, 2005 now abandoned, which is itself a National Phase of International Application No. PCT/EP2004/001543 filed on Feb. 18, 2004 and claiming benefit of Great Britain Application Nos. 0303867.6 filed Feb. 19, 2003 and 0320195.1 filed Aug. 28, 2003, all of which are incorporated fully herein by reference.

FIELD OF THE INVENTION

The present invention relates to vaccines for protecting fish against nodavirus infection, to processes for manufacturing such vaccines, and to use of these vaccines in preventing Viral Nervous Necrosis.

BACKGROUND OF THE INVENTION

Beta-nodaviruses are single-stranded RNA, non-enveloped virions and are the etiological agents of Viral Nervous Necrosis (VNN) or fish encephalitis, a disease characterized by the development of a vacuolating encephalopathy and retinopathy, and the presence of virus-like particles in neurons of infected fish. VNN represents a significant barrier to commercial aquaculture activities because of the frequency of incidence of the disease, the high levels of mortality (approaching 100%) and its widespread distribution across warmwater and coldwater farmed fish species.

Chemical disinfection to destroy nodavirus in isolated bodies of water based on chlorine, iodine or ammonium is the standard preventative method, but a vaccine would be preferred due to concerns about the effects of such chemicals on the marine environment. At present there is no commercially available vaccine for protecting fish against nodavirus infections, and specifically against VNN. It is an object of the present invention to provide a vaccine which confers commercially significant protection on farmed fish against nodavirus infection.

SUMMARY OF THE INVENTION

In a first aspect of the invention there is provided a vaccine against VNN comprising inactivated piscine nodavirus.

In a second aspect of the invention there is provided a method of preparing a piscine nodavirus vaccine, comprising inactivating the virus using an aziridine compound.

In a third aspect of the invention there is provided a method of treating or preventing VNN comprising administering to a fish in need of such treatment a vaccine comprising inactivated piscine nodavirus.

In another aspect of the invention there is provided use of inactivated nodavirus in the manufacture of a medicament for the prevention or treatment of nodavirus infection or VNN.

In a further aspect of the invention there is provided fish to which a vaccine comprising inactivated piscine nodavirus has been administered.

In yet another aspect of the invention there is provided Viral Nervous Necrosis Virus strain Mt/01/Sba deposited with the ECACC on Jun. 4, 2003 under Accession No. 03060401, or a strain with similar identifying characteristics. A strain with similar identifying characteristics is one which serologically reacts with antiserum raised against deposited nodavirus strain Mt/01/Sba.

DETAILED DESCRIPTION OF THE INVENTION

Recent approaches to developing a nodavirus vaccine for fish have relied on recombinantly produced viral protein. We chose to compare two candidate vaccines, one based on adjuvanted recombinant nodavirus capsid protein, and the other an inactivated viral preparation. The virus was inactivated using binary ethyleneimine, and was administered in admixture with Freund's incomplete adjuvant.

The recombinant protein vaccine failed to provide significant protection following challenge with live virus. In contrast, the killed virus proved to be highly efficacious (Relative Percentage Survival=91.6%). This was surprising: the prevailing view in the field is that inactivated vaccines fail to protect fish against nodavirus, at least in sea bass (International Council for the Exploration of the Sea, Mariculture Committee: Report on the Working Group on Pathology and Diseases of Marine Organisms, Copenhagen, Denmark, 12-16 March 2002).

According to the invention, a process for the production of a vaccine against a nodavirus starts with infecting suitable culture cells with a virulent strain of the virus in question. The method comprises the steps of 1) infecting a susceptible cell line with a piscine nodavirus; 2) allowing said nodavirus to grow in a growth-supporting media until a cytopathic effect (CPE) is produced; 3) harvesting said growth-supporting media containing said nodavirus, dead cells, cell debris and infected cells to produce a harvest material; 4) inactivating said harvest material with a suitable inactivating agent; and 5) adjuvanting said inactivated harvest material.

Piscine nodaviruses are commonly cultured in Striped snakehead cells (SNN-1), or SBL from sea bass. SSN-1 is available from the ECACC, Salisbury, UK. Another possibility is the *Epinephelus coioides* grouper cell line disclosed in EP-A-1006178 (GF-1). The cells may comprise a mixed population, or they may be cell clones (such as the E-11 cell line described in Iwamoto et al. (2000) Dis. Aquat. Organ. 43(2): 81-9). The cell line can be grown in Roux bottles, roller bottles or in bioreactors as a suspension culture or on microcarrier beads using any media and serum that supports rapid growth of the cells. The cells are preferably cultivated to form a confluent monolayer and then inoculated with the virus, followed by incubation in a nutrient medium suitable for growth and replication of the virus until the appearance of cytopathic effects (CPE). Leibovitz L-15 medium (Gibco) is an example of an appropriate culture medium, as described by Frerichs et al. (1996) J. Gen. Virol. 77:2067-2071. The preferred sera for cell growth are fetal equine, fetal bovine or calf serum. When the virus has reached its maximum titre, which is variously determined by infectivity, electron microscopy, or other tests conventional in the art, the culture is clarified and filtered, often with centrifugation, such as CsCl density gradient centrifugation, to remove the cells and cell debris, after which the supernatant fluids may be concentrated by ultrafiltration.

The virulent virus resulting from purification is ready for inactivation. As used herein, the term "inactivated virus" refers to previously virulent virus which has undergone treatment to inactivate, kill or otherwise modify the virus to substantially eliminate its virulent properties while retaining its characteristic property of immunogenicity. According to the invention the virus can be inactivated by addition of an aziridine compound, which may be monomeric (e.g. ethyleneimine) or oligomeric. The preferred aziridine compound is binary ethyleneimine (BEI). Other examples are trimeric ethyleneimine (TEI) and acetyl-ethyleneimine.

According to one method of inactivation, BEI can be prepared by dissolving, to a concentration of 0.1 M, 2-bromoethylamine hydrobromide (BEA) in approximately 0.2 N sodium hydroxide solution, and incubating at 37° C. for 1 hour.

The BEI formed in this way by cyclisation is then added to a virus suspension, the process of inactivation generally requiring a period of at least several hours, preferably at a BEI concentration of from about 0.001 to about 0.01M, most preferably between about 0.003 to about 0.005M, and optimally about 0.004M. During inactivation the culture is held at normal temperature/room temperature. For instance, an inactivation step in 0.004M BEI at 25° C. for 72 hours may be appropriate. In the absence of further adjustment the pH of the culture medium tends to become more acid over time. Accordingly the pH of the culture medium is optionally monitored continuously during the inactivation process and maintained at the desired mildly alkaline or mildly acidic level by the addition of further alkali as required. After inactivation any residual BEI in the harvest can be neutralised by adding an excess amount of a suitable reagent such as citric acid or sodium thiosulphate solution.

Ethyleneimine can be prepared by addition of 2-aminoethyl hydrogen sulphate to a boiling sodium hydroxide solution, and is also available commercially. Acid induced polymerization of ethyleneimine produces different oligomeric ethyleneimines; selected oligomers can be isolated from the reaction mixture by fractional distillation. In a manner similar to BEI, ethyleneimine and its oligomer forms are mixed with a viral suspension and incubated in order to effect inactivation.

For best results the viral inactivation step is carried out at a temperature in the range of about 15 to about 35° C., preferably about 20 to about 27° C., and more preferably about 24-26° C., optionally at about 25° C.

In order to confirm inactivation, the inactivated viral preparation is incubated with susceptible host cells for several days, for instance as described in the Examples, and observed for CPE.

Preservatives such as thimerosal can be added to the inactivated fluids, and the inactivated material may be adjuvanted. After adjuvanting, stabilizers such as glycerol/EDTA can be added to improve antigen stability. The virus fluids may be further concentrated using ultrafiltration, polyethylene glycol precipitation or polyethylene oxide adsorption. These concentrated antigens can be kept at −70° C. or lower temperatures for many years, if necessary, and made into vaccine when required by dilution in a suitable buffer and optional addition of adjuvants.

In a preferred embodiment the inactivated viral supernatant is admixed with a pharmaceutically acceptable carrier, and optionally with an adjuvant.

The prime targets of the vaccine of the invention are extremely diverse, being any marine or freshwater species which is susceptible to infection by piscine beta-nodaviruses. A non-exhaustive list includes: Sea bass (*Dicentrarchus labrax* L.), Sea bream (*Sparus aurata*), Umbrina (*Umbrina cirrosa*), Atlantic halibut (*Hippoglossus hippoglossus*), Winter flounder (*Pleuronectes americanus*), Atlantic cod (*Gadhus morhua*), Haddock (*Melanogramus aeglefinus*), Dover sole (*Solea solea*), Turbot (*Scophthalmus maximus*), Jack fish (e.g. striped jack, *Pseudocaranx dentex*), Grouper (e.g. sevenband grouper/*Epinephelus septemfasciatus*, redspotted grouper/*Epinephelus akaara*, greasy grouper/*Epinephelus tauvina*, carpet cod/*Epinephelus fuscogutatus*, humpback grouper/*Cromileptes altivelis*, blackspotted grouper/*Epinephelus malabaricus*, kelp grouper/*Epinephelus moara*, and marbled leopard grouper/*Plectropomus maculates*), Wolffish (*Anarhicas minor*), Barramundi (*Lates calcarifer*), tiger puffer (*Takifugu rubripes*), Japanese flounder (*Paralichthys olivaceus*), rock porgy (*Oplegnathus punctatus*) and Japanese Parrotfish (*Oplegnathus fasciatus*).

Vaccines prepared according to the invention can comprise any inactivated piscine nodavirus, and can achieve protection against any piscine nodavirus. Preferably the virus used to prepare the inactivated vaccine of the invention is selected to be the same strain or of the same genotype as the virus against which protection is sought (although there is likely to be good cross-protection between different genotypes). Piscine nodaviruses can be divided into multiple genotypes based on partial sequence of the coat protein. Non-limiting examples of piscine nodaviruses are: SJNNV (striped jack nervous necrosis virus), RGNNV (redspotted grouper nervous necrosis virus), TPNNV (tiger puffer nervous necrosis virus), BFNNV (barfin flounder nervous necrosis virus), FEV (fish encephalitis virus), MGNNV (*malabaricus* grouper nervous necrosis virus), DGNNV (dragon grouper nervous necrosis virus), Atlantic halibut nodavirus, sea bass encephalitis virus, *Lates calcarifer* encephalitis virus, Maltese sea bass nodavirus, and GGNNV (greasy grouper nervous necrosis virus).

Strains of nodavirus are available from depositary institutions and laboratories around the world, including the Community Reference Laboratory for Fish Diseases at the Danish Veterinary Institute in Århus. Examples are GNNV strain MT9410, SJNNV strain SJNag93, RGNNV strain SGWak97, RGNNV strain SGMie95, TPNNV strain TPKag93, BFNNV strain JFIWa98, Halibut nervous necrosis virus isolates AHNor96 and AH99NorA, *Umbrina cirrosa* nodavirus isolate Uc-1, Atlantic halibut nodavirus isolate AH95NorA, and Japanese flounder nervous necrosis virus isolate JF-HI93. Maltese nodavirus isolate Mt/01/Sba is a preferred strain for use in the present invention. This strain was deposited under the Budapest Treaty at the European Collection of Cell Cultures (ECACC) at Porton Down, Salisbury, Wiltshire SP4 0JG, UK, on Jun. 4, 2003 and assigned Accession Number 03060401. The source of this strain is the Institute of Aquaculture at the University of Stirling. Nodavirus strains with similar identifying characteristics preferred for use in the invention can be identified by specific cross-reaction with antiserum or purified polyclonal or monoclonal antibodies raised against strain Mt/01/Sba.

The vaccine of the invention provides protection against nodavirus infection and related disease to a degree which is commercially significant and valuable for the fish farming industry. Given that nodavirus infections typically kill nearly 100% of all infected fish in the field, any treatment resulting in an increase in relative percentage survival (RPS) is an improvement over conventional treatment methods. In commercial terms, significant protection usually means an RPS for vaccinated fish of at least about 30%, more preferably at least about 40%, more preferably at least 50%, more preferably at least 60%, for instance at least 70%. The vaccine of the invention may be used prophylactically, or may be administered as a treatment to nodavirus infected fish to eliminate the infection and/or improve recovery rates.

In some instances a population of fish of a certain species or of a certain age may not develop any disease symptoms when they are exposed to nodavirus. However, they may act as carriers for the virus, and the risk remains that they may pass the virus to fish which are vulnerable. It is also an aspect of the invention to vaccinate clean brood-stock fish against nodavirus using the inactivated virus disclosed herewith to prevent them from becoming carriers.

In a particular embodiment, the invention provides use of an inactivated piscine nodavirus in the manufacture of a vaccine for the prevention or treatment of VNN in Atlantic cod, by vaccinating co-cultivated salmonid fish (such as coho salmon (*Oncorhynchus kisutch*), chinook salmon (*Oncorhynchus tshawytscha*), masu salmon (*Oncorhynchus masou*), pink salmon (*Oncorhynchus gorbuscha*), rainbow trout (*Oncorhynchus mykiss*), and Atlantic salmon (*Salmo salar*)). Also provided is a method of preventing VNN in Atlantic cod, comprising administering to co-cultivated salmonid fish a vaccine comprising an inactivated piscine nodavirus.

In one embodiment the vaccine of the invention is administered to larvae and/or juveniles of a fish species, such as juveniles of sea bass. Alternatively, the vaccine can be administered to adult or mature fish.

The typical routes of administration of the vaccine are by injection into the peritoneal cavity (for larger fish), intramuscular injection, orally in feed, or by immersion in seawater or in fresh water. It is recommended that fish be 5 grams or greater in body weight for administration of the vaccine of the invention by injection. A suitable injection volume is about 10 to about 200 µl, preferably about 50 to about 100 µl. For immersion or oral administration, a body weight of at least 1 gram is preferred.

The effective dosage of vaccine may vary depending on the size and species of the subject, and according to the mode of administration. The optimal dosage can be determined through trial and error by a veterinarian or aquaculture specialist. A suitable dosage range of virus is from about $10^2$ to $10^9$ $TCID_{50}$ (tissue culture infectious dose affecting 50% of cultures inoculated) per unit dose, preferably about $10^4$ to $10^8$ $TCID_{50}$ per unit dose, more preferably about $10^6$ to $10^7$ $TCID_{50}$ per unit dose, most preferably about $10^7$ $TCID_{50}$ per unit dose. Preferably a single dosage unit is administered to the fish to be treated. Smaller fish may benefit from a dose of about $10^4$ to $10^7$ $TCID_{50}$/ml with dip (immersion) administration, for instance with a contact time of about 60 seconds.

Typically, vaccines are prepared as liquid solutions, emulsions or suspensions for injection or delivery in water. For instance, a liquid emulsion or emulsifiable concentrate can be prepared in order to be added to a water tank or bath where the fish are held. Solid (e.g. powder) forms suitable for dissolution in, or suspension in, liquid vehicles, or for mixing with solid food, prior to administration may also be prepared. The vaccine may be a lyophilised culture in a ready to use form for reconstitution with a sterile diluent. For instance, lyophilized cells may be reconstituted in 0.9% saline (optionally provided as part of the packaged vaccine product). A preferred formulation of injectable vaccine is an emulsion. Liquid or reconstituted forms of the vaccine may be diluted in a small volume of water (e.g. 1 to 100 volumes) before addition to a pen, tank or bath. The pharmaceutical vaccine compositions of the invention may be administered in a form for immediate release or extended release.

Pharmaceutically acceptable carriers or vehicles with which the inactivated virus can be admixed include conventional excipients, and may be, for example, aqueous solvents such as water, saline or PBS, oil, dextrose, glycerol, wetting or emulsifying agents, bulking agents, stabilizers, anti-oxidants, coatings, binders, fillers, disintegrants, diluents, lubricants, pH buffering agents, and the like. Adjuvants such as muramyl dipeptides, avridine, aluminium hydroxide, aluminium phosphate, oils, oil emulsions, saponins, dextran sulphate, glucans, cytokines, block co-polymers, immunostimulatory oligonucleotides and others known in the art may be admixed with the inactivated viral supernatant. A preferred adjuvant is Freund's Incomplete Adjuvant (FIA). The amount of adjuvant added depends on the nature of the adjuvant itself. FIA may advantageously be emulsified with inactivated viral supernatant in a ratio of about 1:1 by volume.

In some instances it may be desirable to combine the vaccine of the invention with another antigen in a combination vaccine, or in a kit comprising both components for separate, sequential or simultaneous administration, for treatment or prevention of VNN or a multitude of diseases to which the fish are susceptible. Other antigens with which the inactivated nodavirus may be combined include antigens from: Iridovirus, VHSV, *Photobacterium damselae* subsp. *piscicida*, *Aeromonas* spp., *Vibrio* spp., *Edwardsiella* spp., *Lactococcus* spp., *Streptococcus* spp., *Flexibacter* spp. and *Nocardia* spp.

EXAMPLES

Preparation of the Inactivated Viral Vaccine

SSN-1 cells are grown in L15 medium (Invitrogen) supplemented with 10% foetal bovine serum (FBS) at 28° C. To subculture these cells, confluent monolayers (4-7 days old) are washed twice using PBS Dulbeccos (Invitrogen) and harvested using trypsin-EDTA (Invitrogen). One flask of cells is routinely split to produce 3 daughter flasks (split ratio 1:3).

To propagate virus for this study, a confluent 75 cm² flask of SSN-1 cells is subcultured to produce a 175 cm² flask and a 25 cm² flask. These are incubated at 28° C. until the cells are 70-80% confluent (usually 1 day old). The conditioned media is then aseptically removed and retained and 5 ml of Hanks Balanced Salt Solution (HBSS; Invitrogen) plus 3 ml nodavirus from Maltese sea bass fry (Mt/01/Sba) are added to the 175 cm² flask. The 25 cm² flask is used as a mock (negative control) and has 1 ml conditioned media and 1 ml HBSS+2% FBS only added to it. Flasks are incubated at 25° C. for 30 minutes and then resupplemented as follows:

175 cm² flask—8 ml conditioned media plus 8 ml L15 media only (no FBS).

25 cm² flask—2 ml conditioned media plus 2 ml L15 media only (no FBS).

The final media composition is thus L15+ca. 5% FBS. The reduced serum concentration slows down the growth of the cells to optimize viral replication. Cells are incubated at 25° C. and monitored daily for the development of a cytopathic effect (CPE). When a full CPE is evident, the cell culture supernatant is harvested and centrifuged at 1000 g for 15 minutes at 4° C. to pellet the cell debris. This clarified supernatant, containing the virus, is then treated with binary ethyleneimine (BEI).

Viral Inactivation (1) Cycling of 2-bromoethylamine hydrobromide into binary ethyleneimine. 2.1 g of 2-bromoethylamine hydrobromide is added to 100 ml of 0.175N NaOH to create a 0.1M solution of Binary ethyleneamine (BEA). The solution is placed into a 37° C. water bath for 1-2 hours to create Binary Ethyleneimine (BEI).

(2) Inactivation of virus antigen. 4 ml of 0.1M BEI is added to 96 ml live virus antigen, mixed well and the sample is incubated on a rocking platform at 25° C. for 72 hours (final BEI concentration=4 mM). A positive control is also prepared at this stage containing "live" virus+HBSS only and a negative control consisting of HBSS+BEI.

(3) Neutralisation of BEI. After 72 hours, 40 µl of cold 2M sodium thiosulphate is added per 1 ml of inactivated virus antigen, and inactivation testing is subsequently carried out.

Inactivation Testing

To test that the virus has been successfully inactivated and to determine the $TCID_{50}$ (tissue culture infectious dose affecting 50% of cultures inoculated) of the "live" virus (i.e. positive control sample which has not been treated with BEI), a back titration is carried out on SSN-1 cells in a 96-well plate using the following samples:

(a) Mock=HBSS only
(b) Mock=HBSS+sodium thiosulphate
(c) Mock=HBSS+BEI+sodium thiosulphate
(d) Virus=live virus+HBSS only
(e) Virus=live virus+sodium thiosulphate
(f) Inactivated virus=virus+BEI+sodium thiosulphate
(g) Inactivated virus=virus+BEI+sodium thiosulphate
(h) Inactivated virus=virus+BEI+sodium thiosulphate Samples (a)-(c) act as negative controls and demonstrate the effect these chemicals might have on the cells. Samples (d) and (e) are the positive controls and allow the $TCID_{50}$ to be calculated using the Spearman-Kärber method. Sample (e) also shows whether the sodium thiosulphate alone has an effect on the virus. Samples (f)-(h) are replicates of the inactivated virus and allow to check that the virus is no longer viable.

The 96-well plate is incubated at 25° C. and monitored daily. A final reading is taken after 7-10 days incubation and the $TCID_{50}$ calculated.

The above samples are also simultaneously inoculated into 25 $cm^2$ flasks of SSN-1 cells in L15 media and 5% FBS and incubated at 25° C. After 7 days incubation these cell cultures are passaged onto 1 day-old SSN-1 cells (pre-formed monolayers). A further two successive pre-formed passages are carried out using day 7 supernatant from the previous passaged flask as the inoculum. All of the flasks are monitored for a total of 21 days to check for CPE. All flasks containing BEI treated virus remain negative for CPE (all other controls are as expected); thus, it can be assumed that the virus has been successfully inactivated. Inactivated virus is emulsified 1:1 in Freund's Incomplete Adjuvant (FIA), to a concentration of $10^8$ $TCID_{50}$/ml.

Recombinant Antigen

Recombinant antigen is prepared by cloning the complete coding sequence of the capsid protein from halibut nodavirus strain V9954 into the pET-30EK/LIV vector (Novagen). Following induction of the host cell culture with IPTG, the recombinant capsid protein is harvested as a non-soluble product (inclusion bodies). The recombinant protein is subsequently solubilized, then refolded by performing several rounds of dialysis. The final recombinant antigen is emulsified 1:1 in Freund's Incomplete Adjuvant (FIA), to a final protein concentration of 0.675 mg/ml.

Emulsified vaccines and controls are made by dropping (at about 1 drop $sec^{-1}$) FIA into sterile 15 ml Falcon tubes containing the respective vaccine or control, while vortexing.

Vaccination

Sea bass (*Dicentrarchus labrax*) of mean weight 18 g are kept in tanks of approximately 40 L each, with 60 or 65 fish to a tank. The tanks are supplied with recirculating UV and ozone (when necessary) treated salt-water (35%) system at 23±1° C., and fed commercial sea bass feed (SORGAL S.A., Ovar, Portugal).

After acclimatizing for 7 days in the new holding system and being starved for 24 hours, fish are anaesthetized and immunized with one of the following treatments in duplicated groups by intraperitoneal injection (100 µl/fish): recombinant antigen 1:1 in FIA; BEI inactivated virus 1:1 in FIA, PBS 1:1 in FIA (control); HBSS (Hank's Balanced Salt Solution/Gibco BRL) 1:1 in FIA (control).

Challenge

Fish are challenged at day 24 (552 degree days), after a 24 hour starvation period. Virulent nodavirus inoculum is obtained from a Maltese nodavirus isolate (Mt/01/Sba) originating from farmed sea bass juveniles. Tissue cultures of original harvest are simultaneously inoculated into SSN-1 cells using L-15 medium supplemented with 5% FBS and incubated at 25° C. When CPE is complete, tissue cultures are clarified by centrifugation at 1500 g for 15 min and the supernatant containing virus is re-inoculated (preformed inoculation) into SSN-1 lines in order to achieve a high concentration of virus. After full CPE, tissue cultures are centrifuged (1500 g for 15 min) and stocked at −70° C. until use. SSN-1 cells are then added and incubated with the virus at 25° C. The $TCID_{50}$ (tissue culture infectious dose infecting 50% of inoculated cultures) is calculated according to the method of Spearman-Kärber (1931).

After thawing, the challenge inoculum is diluted in HBSS (Gibco) supplemented with 2% FBS to obtain a challenge dose of $10^7$ $TCID_{50}$ per fish. During anaesthesis, each fish is inoculated i.p. with 100 µl inoculum. The temperature of the tank water is increased to 26° C. 3 days after the challenge to mimic a natural viral outbreak. Brain tissue samples are taken from dead fish to confirm presence of virus.

Results

Specific mortalities start in all groups at day 6 post-challenge, peaking at days 7-8 and decreasing by day 14 post-challenge. The trial is terminated 31 days after challenge. The data obtained are subjected to the 2-Proportion Z-test using a significance level of $P<0.05$.

Significant protection is obtained with the groups vaccinated with BEI inactivated virus, when compared with the respective control groups, while the group vaccinated with the recombinant capsid protein is unprotected.

TABLE 1

Percent survival and relative percent survival of vaccinated groups

| Vaccine | % Mortality Replicate1 | % Mortality Replicate2 | Mean % mortality | RPS (%) | RPS calculated relative to |
|---|---|---|---|---|---|
| PBS 1:1 FIA | 52 | 39 | 45.5 | — | — |
| BEI 1:1 FIA | 4 | 2 | 3 | 91.55 | HBSS 1:1 FIA |
| | | | | 93.71 | PBS 1:1 FIA |
| HBSS 1:1 FIA | 35 | 36 | 35.5 | — | — |
| Recomb 1:1 FIA | 58 | 44 | 51 | 11.80 | PBS 1:1 FIA |

In order to control for possible protective effects of the retrovirus which is present in the SSN-1 cell line a second trial is carried out in an identical manner to the first trial, comparing BEI-inactivated nodavirus with a PBS control as in trial 1 and with an additional control consisting of BEI-inactivated retrovirus emulsified 1:1 in FIA. Table 2 shows the results of this second trial:

TABLE 2

Repeat Trial with inactivated retrovirus control

| Vaccine | % Mortality Replicate1 | % Mortality Replicate2 | Mean % mortality | RPS (%) | RPS calculated relative to |
|---|---|---|---|---|---|
| PBS 1:1 FIA | 72 | 46 | 59 | — | — |
| BEI nodavirus 1:1 FIA | 15 | 7 | 11 | 77 | BEI retrovirus 1:1 FIA |
|  |  |  |  | 82 | PBS 1:1 FIA |
| BEI retrovirus 1:1 FIA | 42 | 48 | 45 | 24 | PBS 1:1 FIA |

Although the RPS for the BEI-inactivated nodavirus vaccine is lower (77%) in trial 2 than when compared with HBSS in the first trial (91.95%) the challenge is stronger (PBS control in trial 1 had mortality of 45.5%, compared with 59.26% in trial 2).

These challenge experiments show that, contrary to all expectations, a piscine nodavirus inactivated using an aziridine compound (BEI) can be remarkably effective in preventing mortalities in sea bass associated with nodavirus infection. The specific mechanisms of inactivation of viruses using different agents are still poorly understood, and in particular the effects of inactivation using aziridine compounds on immunogenicity of nodaviruses could not have been predicted, given the sparseness of knowledge in this field. The findings of the Examples are particularly surprising in view of the reported failure of inactivated nodavirus to protect fish against VNN.

The invention claimed is:

1. An inactivated piscine viral nervous necrosis virus (NNV) strain Mt/01/Sba deposited with the ECACC under Accession No. 03060401, wherein the inactivated piscine viral nervous necrosis virus when administered to fish, is capable of providing a relative percent survival (RPS) of at least 50% after challenge with a non-inactivated NNV strain of Mt/01/Sba, and wherein the inactivated piscine viral nervous necrosis virus is inactivated with binary ethyleneimine.

2. A vaccine composition comprising:
   an inactivated piscine viral nervous necrosis virus (NNV) strain Mt/01/Sba deposited with ECACC under Accession No. 03060401; and
   a pharmaceutically acceptable carrier,
   wherein the inactivated piscine viral nervous necrosis virus is inactivated with binary ethyleneimine.

3. The vaccine composition of claim 2, wherein the vaccine is capable of providing a relative percent survival (RPS) of at least 77% in a fish population vaccinated with the vaccine subsequent to challenge with a non-inactivated NNV strain of Mt/01/Sba.

4. The vaccine composition of claim 3, wherein the RPS is at least 91.55%.

5. The vaccine composition of claim 2, further comprising about $10^2$ to about $10^9$ TCID$_{50}$ of the inactivated nodavirus per unit dose.

6. The inactivated piscine viral nervous necrosis virus of claim 1, wherein when administered to fish, is capable of providing a relative percent survival (RPS) of at least 77% after challenge with a non-inactivated NNV strain of Mt/01/Sba.

7. The inactivated piscine viral nervous necrosis virus of claim 1, wherein when administered to fish, is capable of providing a relative percent survival (RPS) of at least 91% after challenge with a non-inactivated NNV strain of Mt/01/Sba.

8. The vaccine composition of claim 2, further comprising an adjuvant.

* * * * *